United States Patent
Wang et al.

(10) Patent No.: US 10,605,769 B2
(45) Date of Patent: Mar. 31, 2020

(54) SENSING DEVICE AND BIOLOGICAL DETECTION METHOD

(71) Applicant: National Tsing Hua University, Hsinchu (TW)

(72) Inventors: Yu-Lin Wang, Hsinchu (TW); Yen-Wen Chen, Nantou County (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 15/864,003

(22) Filed: Jan. 8, 2018

(65) Prior Publication Data

US 2019/0107507 A1    Apr. 11, 2019

(30) Foreign Application Priority Data

Oct. 5, 2017  (TW) .............................. 106134426 A

(51) Int. Cl.
*G01N 27/414*  (2006.01)
*A61B 5/0478*  (2006.01)
*G01N 27/327*  (2006.01)

(52) U.S. Cl.
CPC ....... *G01N 27/4145* (2013.01); *A61B 5/0478* (2013.01); *G01N 27/4146* (2013.01); *G01N 27/3272* (2013.01)

(58) Field of Classification Search
CPC ............ G01N 27/4145; G01N 27/3272; A61B 5/0478
See application file for complete search history.

(56) References Cited

U.S. PATENT DOCUMENTS 8,129,978 B2    3/2012  Nakazato
8,828,713 B2    9/2014  Ren et al.
(Continued)

FOREIGN PATENT DOCUMENTS

CN    101592627    12/2012
CN    102985813    3/2013
(Continued)

OTHER PUBLICATIONS

Chia-Ho Chu, et al., "Beyond the Debye length in high ionic strength solution: direct protein detection with field-effect transistors (FETs) in human serum," Scientific Reports, vol. 7, Jul. 12, 2017, pp. 1-15.
(Continued)

*Primary Examiner* — Zandra V Smith
*Assistant Examiner* — Andre C Stevenson
(74) *Attorney, Agent, or Firm* — JCIPRNET

(57) ABSTRACT

A sensing device including a transistor, at least one response electrode, and a receptor is provided. The transistor includes a gate end, a source end, a drain end, and a semiconductor layer. The source end and the drain end are located on the semiconductor layer, and the gate end is located between the source end and the drain end. The at least one response electrode is disposed opposite to the gate end of the transistor and spaced apart from the transistor. The receptor is bonded onto the at least one response electrode. When a voltage is applied to the at least one response electrode, an electric field between the at least one response electrode and the gate end of the transistor is F, and F≥1 mV/cm.

21 Claims, 6 Drawing Sheets

(56) References Cited

U.S. PATENT DOCUMENTS

| | | | |
|---|---|---|---|
| 2003/0047450 A1* | 3/2003 | Yang | B01J 19/0093 |
| | | | 204/403.01 |
| 2005/0249667 A1* | 11/2005 | Tuszynski | A61B 8/08 |
| | | | 424/9.3 |
| 2010/0159461 A1* | 6/2010 | Toumazou | G01N 27/4148 |
| | | | 435/6.11 |
| 2017/0016916 A1 | 1/2017 | Wang et al. | |
| 2017/0371464 A1* | 12/2017 | Nakanishi | G06F 3/0412 |

FOREIGN PATENT DOCUMENTS

| | | |
|---|---|---|
| CN | 103675073 | 3/2014 |
| TW | 200638034 | 5/2007 |
| TW | 201634919 | 10/2016 |
| TW | I565946 | 1/2017 |

OTHER PUBLICATIONS

"Office Action of Taiwan Counterpart Application", dated Nov. 19, 2018, p. 1-p. 3.

\* cited by examiner

SENSING DEVICE AND BIOLOGICAL DETECTION METHOD

CROSS-REFERENCE TO RELATED APPLICATION

This application claims the priority benefit of Taiwan application serial no. 106134426, filed on Oct. 5, 2017. The entirety of the above-mentioned patent application is hereby incorporated by reference herein and made a part of this specification.

BACKGROUND OF THE INVENTION

1. Field of the Invention

The invention relates to a detection device and a method thereof. More particularly, the invention relates to a sensing device and a biological detection method.

2. Description of Related Art

In the applications of biomedical science and genomics, quantitative measurement of specific deoxyribonucleic acid (DNA) or ribonucleic acid (RNA) is crucial. In order to realize a rapid detection technology which is not limited to laboratory testing, a metal oxide semiconductor field effect transistor (MOSFET) is currently used as a biosensor to quantify a DNA concentration in a test solution. For instance, when a detection is performed, a fixed bias may be provided to the biosensor, and that different current changes are generated in the biosensor owing to different concentrations of DNA or RNA. Therefore, after a calibration curve is established through measuring the known DNA or RNA concentration, an unknown DNA or RNA content in the test solution can be inferred.

Nevertheless, the test solution usually contains a high concentration of salt (e.g., blood in the human body) in practice. Furthermore, in an existing biosensor, a fixed voltage is only provided when a reaction is balanced (e.g., a reaction between a receptor in the biosensor and a ligand in the test solution is balanced). At this time, a screening effect is generated due to high concentration of salt, and measurement is thereby influenced and can not be performed. As such, a method is adopted for the time being in which the test solution is diluted before performing the detection. Influences caused by the screening effect may thereby be solved. Nevertheless, as the test solution is overly diluted, a detection limit and a sensitivity of the existing biosensor are not sufficient enough to measure the actual concentration of DNA or RNA in the test solution accurately.

In light of the above, how to develop a sensing device with a low detection limit and a high sensitivity is one of the important issues to be addressed by those skilled in the art.

SUMMARY OF THE INVENTION

The invention provides a sensing device and a biological detection method, which provide characteristics of the low detection limit and the high sensitivity.

The invention provides a sensing device, which includes a transistor, at least one response electrode, and a receptor. The transistor includes a gate end, a source end, a drain end, and a semiconductor layer, wherein the source end and the drain end are located on the semiconductor layer, and the gate end is located between the source end and the drain end. The at least one response electrode is disposed opposite to the gate end of the transistor and spaced apart from the transistor. The receptor is bonded onto the at least one response electrode. When a voltage is applied to the at least one response electrode, an electric field between the at least one response electrode and the gate end of the transistor is F, and F≥1 millivolt/centimeter.

According to an embodiment of the invention, the at least one response electrode is a plurality of response electrodes, and the response electrodes are spaced apart from each other.

According to an embodiment of the invention, a plurality of switch circuits are further included. Each of the response electrodes is connected to the corresponding switch circuit.

According to an embodiment of the invention, the at least one response electrode is separately disposed above the gate end of the transistor.

According to an embodiment of the invention, the at least one response electrode and the gate end of the transistor are located on a same plane.

According to an embodiment of the invention, the transistor includes a high electron mobility transistor, a silicon-based field effect transistor, a nanowire field effect transistor, a carbon nanotube field effect transistor, a graphene field effect transistor or a molybdenum disulfide field effect transistor.

According to an embodiment of the invention, the receptor includes an antibody, an aptamer, or a combination thereof.

According to an embodiment of the invention, a surface on which the at least one response electrode and the receptor are bonded to each other is formed by gold.

The invention also provides a biological detection method, which includes the following steps. A sensing device is provided, wherein the sensing device includes a transistor, at least one response electrode, and a receptor, the at least one response electrode is disposed opposite to the gate end of the transistor and spaced apart from the transistor, and the receptor is located on the at least one response electrode. A test solution is placed on the at least one response electrode, wherein a target substance capable of generating a reaction with the receptor in the test solution is combined thereon. A voltage is applied to the at least one response electrode to generate an electric field between the at least one response electrode and the gate end of the transistor, and a current generated from the transistor is measured to obtain a content of the target substance in the test solution, wherein the electric field is F, and F≥1 millivolt/centimeter.

According to an embodiment of the invention, after placing the test solution onto the at least one response electrode, the method further includes enabling the target substance and the receptor to perform a hybridization reaction at a hybridization temperature.

According to an embodiment of the invention, after applying a voltage to the at least one response electrode, the method further includes enabling the target substance and the receptor to perform a dehybridization reaction at a dehybridization temperature.

According to an embodiment of the invention, wherein the dehybridization temperature is greater than the hybridization temperature, and the hybridization temperature is less than or equal to $T_m$ values of the receptor and the target substance.

According to an embodiment of the invention, the at least one response electrode is a plurality of response electrodes, and the response electrodes are spaced apart from each other.

According to an embodiment of the invention, a plurality of switch circuits are further included. Each of the response electrodes is connected to the corresponding switch circuit.

According to an embodiment of the invention, the at least one response electrode is separately disposed above the gate end of the transistor.

According to an embodiment of the invention, the at least one response electrode and the gate end of the transistor are formed on a same plane.

According to an embodiment of the invention, the transistor includes a high electron mobility transistor, a silicon-based field effect transistor, a nanowire field effect transistor, a carbon nanotube field effect transistor, a graphene field effect transistor or a molybdenum disulfide field effect transistor.

According to an embodiment of the invention, the receptor includes an antibody, an aptamer, or a combination thereof.

According to an embodiment of the invention, a surface on which the at least one response electrode and the receptor are bonded to each other is formed by gold.

According to an embodiment of the invention, the target substance includes deoxyribonucleic acid (DNA), ribonucleic acid (RNA), or a combination thereof.

Based on the above, in the sensing device and the biological detection method provided by the invention, because the response electrode is disposed opposite to the gate end of the transistor and spaced apart from the transistor, and the electric field between the response electrode and the gate end of the transistor is greater than or equal to 1 millivolt/centimeter when a voltage is applied to the response electrode, the sensing device can have the characteristics of the low detection limit and the high sensitivity. Further, because the receptor may be specifically combined with the target substance to be detected, the sensing device can provide a high selectivity for the target substance to be measured.

To make the aforementioned and other features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
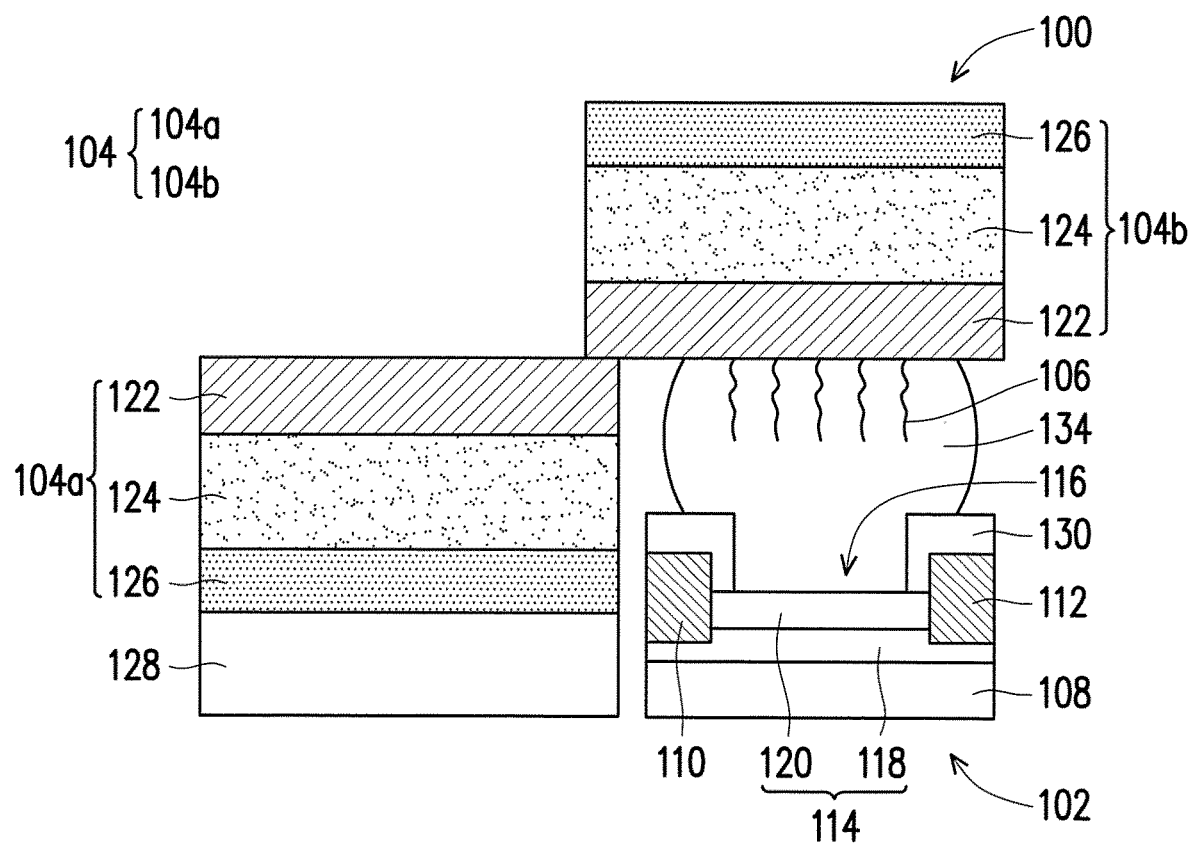
FIG. 1 is a schematic side view of a sensing device according to an embodiment of the invention.

The invention will be described more comprehensively below with reference to the drawings for the embodiments. However, the invention may also be implemented in different forms rather than being limited by the embodiments described in the invention. Thicknesses of layer and region in the drawings are enlarged for clarity. The same reference numbers are used in the drawings and the description to indicate the same or like parts, which are not repeated in the following embodiments Further, the language used to describe the directions such as up, down, left, right, front, back or the like in the reference drawings is regarded in an illustrative rather than in a restrictive sense. Thus, the language used to describe the directions is not intended to limit the scope of the invention.

Figure 2:
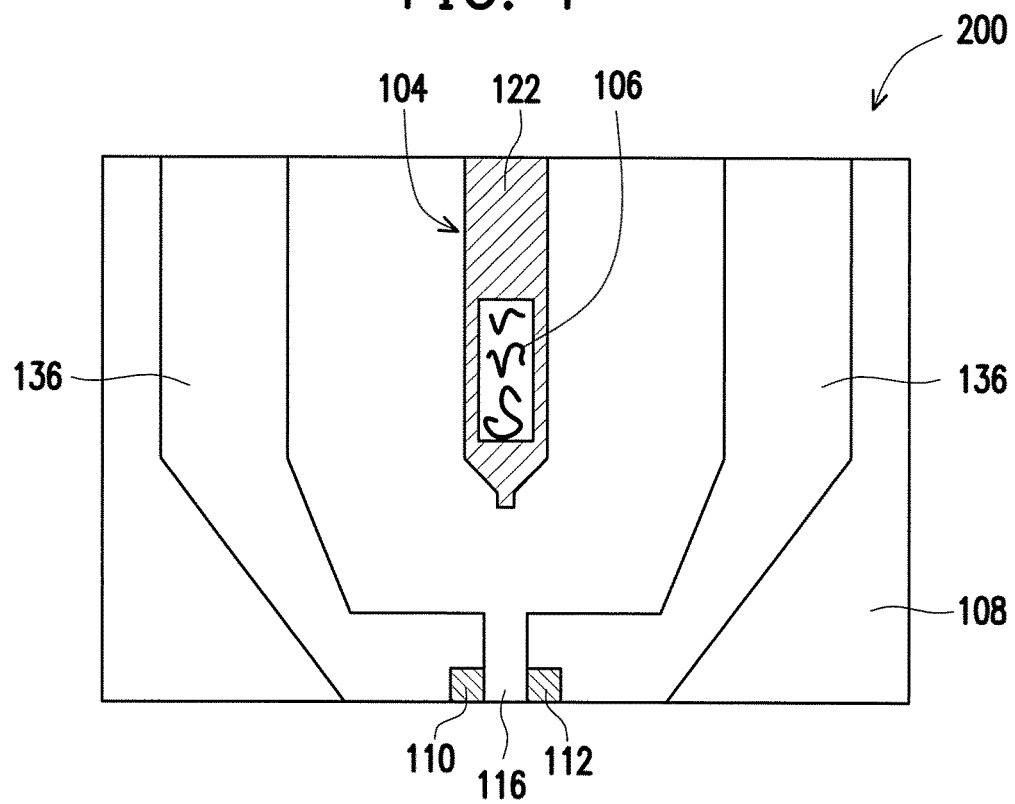
FIG. 2 is a schematic top view of a sensing device according to another embodiment of the invention.

FIG. 1 is a schematic side view of a sensing device according to an embodiment of the invention. FIG. 2 is a schematic top view of a sensing device according to another embodiment of the invention.

With reference to FIG. 1, a sensing device 100 includes a transistor 102, at least one response electrode 104, and a receptor 106. In some embodiments, the sensing device 100 is applicable to detect a deoxyribonucleic acid (DNA) content or a ribonucleic acid (RNA) content in a test solution, but the invention is not limited thereto. In other embodiments, the sensing device 100 may also be used to detect contents of other Bio-targets.

The transistor 102 may include a substrate 108, a source end 110, a drain end 112, a semiconductor layer 114, and a gate end 116. The transistor 102 is, for example, a high electron mobility transistor (HEMT), a silicon-based field effect transistor, a nanowire field effect transistor, a carbon nanotube field effect transistor, a graphene field effect transistor, or a molybdenum disulfide field effect transistor.

The semiconductor layer 114 is located on the substrate 108. A material of the substrate 108 is, for example, silicon, sapphire, or a combination thereof. A material of the semiconductor layer 114 is, for example, GaN, AlInN, AlGaN, or a combination thereof. In some embodiments, the transistor 102 is the high electron mobility transistor, in which the semiconductor layer 114 is composed of a GaN layer 118 and an AlInN layer 120 located thereon. In this case, due to a low dimensional heterogeneous structure interface between the GaN layer 118 and the AlInN layer 120, the transistor 102 can provide an excellent carrier transmission characteristic. In some other embodiments, other materials with piezoelectricity such as AlGaN may also be used to replace the AlInN layer 120. In other words, in the semiconductor layer 114, materials of layers formed on the GaN layer 118 are not limited only to be AlInN, and instead, the other materials with piezoelectricity may also be used. In some embodiments, a size of the AlInN layer 120 is less than that of the GaN layer 118. In other words, a part of a top surface of the GaN layer 118 is exposed to be in contact with the source end 110 and the drain end 112 located thereon. In some embodiments, the semiconductor layer 114 may be formed on the substrate 108 by a physical vapor deposition (PVD) or a chemical vapor deposition (CVD).

The source end 110 and the drain end 112 are located on the semiconductor layer 114, and the gate end 116 is located between the source end 110 and the drain end 112. In some embodiments, the source end 110 and the drain end 112 are respectively located on two opposite sidewalls of the AlInN layer 120 and on the top surface of the GaN layer 118. In some embodiments, materials of the source end 110 and the drain end 112 may include one or more than one conductive material, and said conductive material may be, for example, a metallic material, a metallic compound, or a combination thereof. The metallic material may be, for example, Ti, Al, Ni, Au, W, or a combination thereof; the metallic compound may be, for example, TiN, TiW, TiWN, WN, or a combination thereof. A forming method of the source end 110 and the drain end 112 may be, for example, a chemical vapor deposition, a physical vapor deposition, or other suitable forming methods.

The response electrode 104 is disposed opposite to the gate end 116 of the transistor 102 and spaced apart from the transistor 102, and the response electrode 104 is not electrically connected to the gate end 116. In some embodiments, when a voltage is applied to the response electrode 104, an electric field F is generated between the response electrode 104 and the gate end 116 of the transistor 102. In some embodiments, the electric field F is greater than or equal to 1 millivolt/centimeter (F≥1 mV/cm). In this way, when the applied electric field F is within aforesaid range, the sensing device 100 is capable of surpassing Nernst limit to provide lower detection limit and higher sensitivity. In addition, in some embodiments, the response electrode 104 may include a response layer 122, a silicon nitride layer 124, and a base 126.

The response layer 122 is disposed opposite to the gate end 116 of the transistor 102 and spaced apart from the transistor 102 above the gate end 116 of the transistor 102. In some embodiments, the response layer 122 may include materials such as metal, a nano material, or a conductive polymer to improve sensitivity, detection limit, stability, or selectivity for the sensing device 100. For instance, the response layer 122 may contain a nano particle or a carbon nanotube to improve the sensitivity or the detection limit of a biological detection; the response layer 122 may also be composed of gold (Au) (i.e., a surface on which the response electrode 104 and the receptor 106 are bonded to each other is formed by gold). In this case, due to the bonding which is easily generated between gold and the receptor 106, the receptor 106 may be stably bonded onto the response electrode 104, so as to improve the stability of the sensing device 100.

The silicon nitride layer 124 is located between the response layer 122 and the base 126. In this way, in the detection, the silicon nitride layer 124 can block electrons generated by the response layer 122 in the detection from being transferred to the base 126, so as to reduce measurement deviation. A material of the base 126 is, for example, silicon, but the invention is not limited thereto.

In some embodiments, the response electrode 104 may be composed of a first sub-electrode 104a and a second sub-electrode 104b, which are structurally identical and oppositely connected to each other. For example, the first sub-electrode 104a is disposed on a glass substrate 128 in a direction away from the base 126 with respect to the response layer 122, and a sum of heights of the first sub-electrode 104a and the glass substrate 128 is greater than a height of the transistor 102. Then, the response layer 122 of the second sub-electrode 104b and the response layer 122 of the first sub-electrode 104a are connected to each other by having the response layer 122 of the second sub-electrode 104b protruded out of the first sub-electrode 104a, such that the response layer 122 of the second sub-electrode 104b is located above the gate end 116 of the transistor 102 and a gap interval is formed between the response layer 122 of the second sub-electrode 104b and the gate end 116. That is to say, the response electrode 104 is separately disposed above the gate end 116 of the transistor 102. In some other embodiments, the response electrode 104 may also be formed as one piece.

The receptor 106 is bonded onto the at least one response electrode 104. In this case, due to a characteristic of the receptor 106 which can be specifically combined with the target substance to be detected, the target substance to be detected and the receptor 106 on the response electrode 104 are thereby combined, so as to lower influences from other interferences in a test solution 134, and the sensing device 100 can thus provide high selectivity for the target substance to be measured. The receptor 106 can be bonded onto the entire response electrode 104 or be bonded onto a part of the response electrode 104, and the invention is not limited thereto. The receptor 106 may be, for example, an antibody, an aptamer, or a combination thereof. In some embodiments, the receptor 106 may be a DNA probe, a ssDNA probe, or a combination thereof. In some embodiments, when the target substance is DNA, the receptor 106 is a DNA probe; when the target substance is RNA, the receptor 106 is a ssDNA probe, but the invention is not limited thereto. Other suitable receptors may be selectively used according to different target substances, as long as the target substance can be specifically combined with the corresponding receptor. The RNA may be microRNA (miRNA), such as miR-126, miR-21, or miR-208a.

In some embodiments, top surfaces and sidewalls of the source end 110 and the drain end 112 may also be selectively covered by a protective layer 130 to improve a stability of the transistor 102. A material of the protective layer 130 may be, for example, a photoresist material (e.g., SU8).

FIG. 2 is a schematic top view of a sensing device according to another embodiment of the invention. A sensing device 200 shown in FIG. 2 is similar to the sensing device 100 shown in FIG. 1, the difference between the two is that, the response electrode 104 and the gate end 116 of the transistor 102 are located on a same plane, and a AlGaN layer is formed on the GaN layer 118 of the transistor 102. Detailed description regarding the rest of identical or similar components has been provided above, which is not repeated hereinafter.

With reference to FIG. 2, in the sensing device 200, the response electrode 104 can be located on the same plane with the gate end 116 of the transistor 102 and disposed opposite to and spaced apart from each other by extending the substrate 108 of the transistor 102 and disposing the response electrode 104 on the substrate 108. In this embodiment, the receptor 106 covers a part of the response electrode 104, and the source end 110 and the drain end 112 are connected to external electronic devices (not shown) respectively by wires 136.

Figure 3:
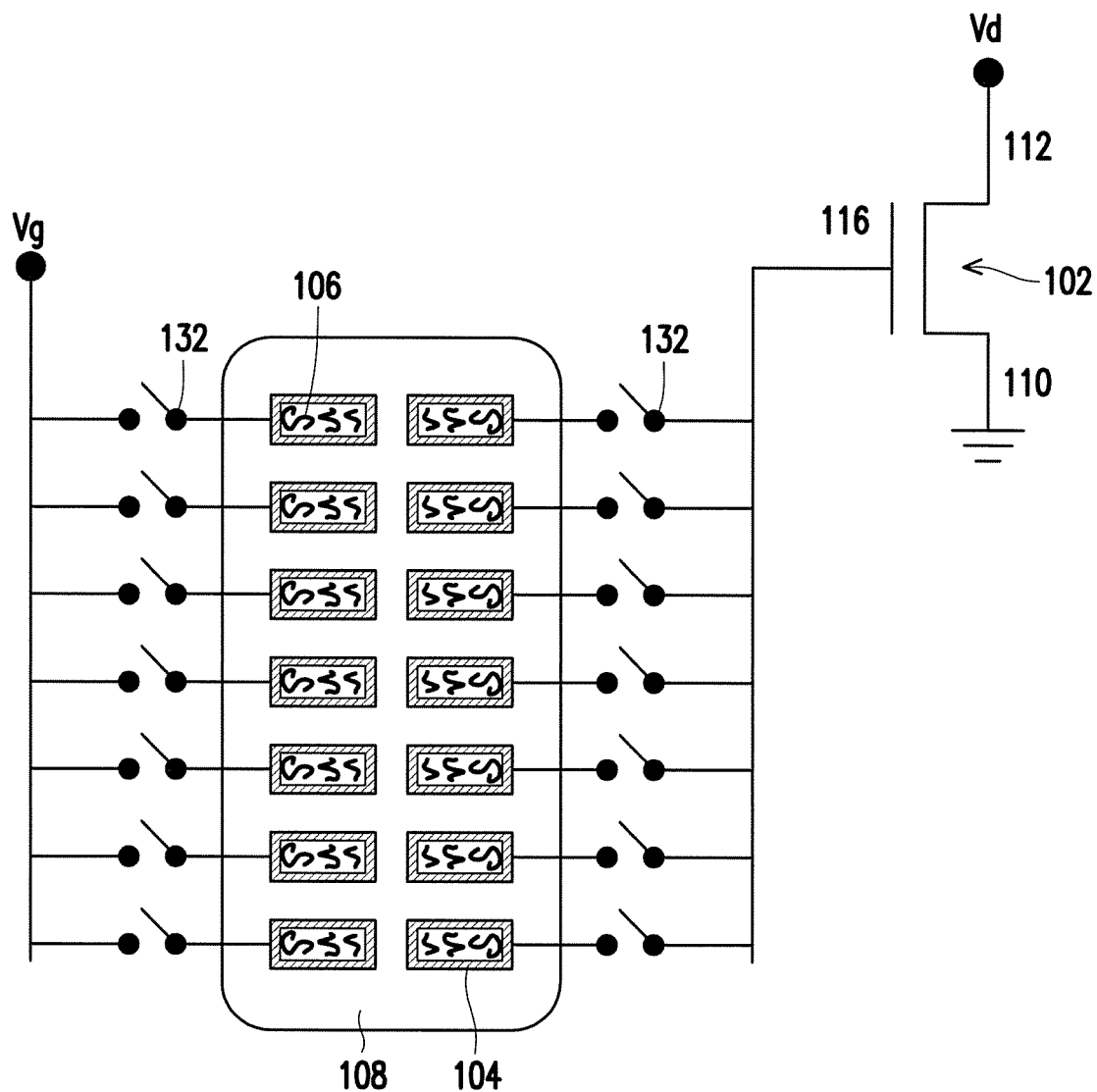
FIG. 3 is a schematic top view of a sensing device according to yet another embodiment of the invention.

FIG. 3 is a schematic top view of a sensing device according to yet another embodiment of the invention. A sensing device 300 shown in FIG. 3 is similar to the sensing device 200 shown in FIG. 2, the difference between the two is that, the sensing device 300 has a plurality of response electrodes 104, and the response electrodes 104 are disposed on the substrate 108 and spaced apart from each other. Detailed description regarding the rest of identical or similar components has been provided above, which is not repeated hereinafter.

With reference to FIG. 3, the sensing device 300 includes the response electrodes 104, wherein the receptors 106 are bonded onto the response electrodes 104, and the response electrodes 104 correspond to the same transistor 102. In this way, the sensing device 300 can simultaneously perform multiple detections on the same or different species of the target substances. As such, not only can a reliability of the detection result be improved, a time required by the detection may be reduced. In addition, because the response electrodes 104 share the same transistor 102 and the next detection may be performed simply by replacing the used response electrode 104, a cost required by the detection may be lowered. In some embodiments, the sensing device 300 further includes a plurality of switch circuits 132, and each of the response electrodes 104 is connected to the corresponding switch circuit 132. Accordingly, the desired response electrode 104 to be used may be selectively controlled such that the sensing device 300 is applicable to various measuring means. For example, the same target substance may be detected at different times, so as to observe a variation in concentration and time. In some embodiments, the switch circuits 132 are located on two opposite sides of the response electrodes 104. The switch circuits 132 located on one side of the response electrodes 104 are connected to a gate voltage Vg, and the switch circuits 132 located on the other side of the response electrodes 104 are connected to the gate end 116. Further, in the measurement, the source end 110 of the transistor 102 is connected to the ground, and a drain voltage Vd is applied to the drain end 112.

The invention also provides a biological detection method, which is described below by using the sensing device 100 in the foregoing embodiment for a biological detection, but the invention is not limited thereto. In other embodiments, the sensing devices 200 and 300 in other foregoing embodiments may also be used for performing the biological detection. Further, detailed description regarding the connection relationship, the material, the manufacturing process, and the effect of each component in the sensing device 100 has been provided above, which is not repeated hereinafter.

With reference to FIG. 1, the biological detection method includes the following steps. First of all, the sensing device 100 is provided, wherein the sensing device 100 includes the transistor 102, the response electrode 104, and the receptor 106. The response electrode 104 is disposed opposite to the gate end 116 of the transistor 102 and spaced apart from the transistor 102, and the receptor 106 is formed on the response electrode 104.

Next, a test solution 134 is placed on the response electrode 104, such that the target substance capable of generating a reaction with the receptor 106 in the test solution 134 is combined thereon. A volume of the test solution 134 is not particularly limited as long as the test solution 134 can be in contact with the response electrode 104 and the semiconductor layer 114 or the gate end 116 of the transistor 102 (as shown in FIG. 1). In some embodiments, before the test solution 134 is placed onto the response electrode 104, a pretreatment process may also be performed on the test solution 134 so as to remove the interference substance in the test solution 134.

Then, a voltage is applied to the response electrode 104 at a room temperature to generate the electric field F between the response electrode 104 and the gate end 116 of the transistor 102, and a current generated from the transistor 102 is measured to obtain a content of the target substance in the test solution 134. In some embodiments, a pulse voltage of which pulse width and height can be adjusted and changed may be applied to the response electrode 104 with the receptor bonded thereon. A voltage difference is thus generated between the response electrode 104 and the gate end 116 spaced apart, and a capacity effect is also generated, thereby a shielding effected is prevented. Accordingly, a concentration of the target substance can be directly measured in a high concentration of salt by the sensing device 100. In addition, sizes of the pulse width and height of the pulse voltage may be adjusted according to a desired detection time to be analyzed by a user and a voltage magnitude required by the detection. For instance, the applied voltage may be a monophasic pulse (drain voltage=2V; gate voltage=0.5V; gate pulse width=0.5 µs) or a biphasic pulse (drain voltage=2V; gate voltage=0.5V; gate cycle pulse width=1 ms). In some embodiments, the electric field F is greater than or equal to 1 millivolt/centimeter (F≥1 mV/cm). In this way, when the applied electric field F is within aforesaid range, the sensing device 100 is capable of surpassing Nernst limit to provide lower detection limit and higher sensitivity.

In some embodiments, after the test solution 134 is placed onto the response electrode 104, a hybridization reaction is performed between the target substance and the receptor 106 at a hybridization temperature, such that an efficiency of combining the target substance with the receptor 106 may be further enhanced. For instance, the hybridization temperature may be less than or equal to $T_m$ values of the receptor 106 and the target substance. In addition, when the hybridization reaction is completed, the temperature may be adjusted back to the room temperature for performing the detection. In this embodiment, the hybridization temperature is 52° C., and such temperature is slightly less than the $T_m$ values of the receptor 106 and the target substance, but the invention is not limited thereto. In other embodiments, the temperature may be adjusted to other suitable temperatures according to different target substance and corresponding receptor 106.

In some embodiments, after the voltage is applied to the response electrode 104 (i.e., after the detection is completed), a dehybridization reaction may be performed between the target substance and the receptor 106 at a dehybridization temperature. As such, the target substance is detached from the receptor 106, and that the next detection can be performed by the sensing device 100. In some embodiments, the dehybridization temperature may be greater than the hybridization temperature or the $T_m$ values. In this embodiment, the dehybridization temperature is 95° C., but the invention is not limited thereto. The temperature may be adjusted to other suitable temperatures according to different target substance and corresponding receptor 106.

In some embodiments, the measured current generated from the transistor may be selectively converted. For example, an integral conversion may be performed on the detected current with respect to the pulse width. In this case, the integral of current versus time is calculated so a total charge accumulated by the source end 110 of the transistor 102 within a specific time may be obtained.

Based on the foregoing embodiments, it can be known that, in the sensing device and the biological detection method proposed in the foregoing embodiments, because the response electrode is disposed opposite to the gate end of the transistor and spaced apart from the transistor, and the electric field between the response electrode and the gate end of the transistor is greater than or equal to 1 mV/cm when a voltage is applied to the response electrode, the sensing device can have the characteristics of the low detection limit and the high sensitivity. Further, because the receptor may be specifically combined with the target substance to be detected, the sensing device can provide a high selectivity for the target substance to be measured.

Hereinafter, the biological detection method and characteristics thereof are described in detail by experimental examples.

EXPERIMENTAL EXAMPLES

Experiment 1 and Experiment 2 are biological detections with the sensing device 200 as exemplary embodiments. Nevertheless, the invention is not limited thereto.

Experiment 1

Figure 4A:
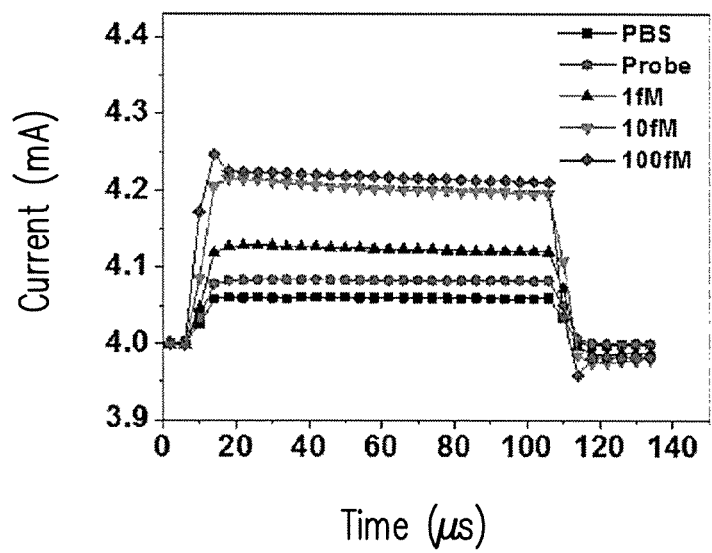
FIG. 4A is a current-time graph obtained by detecting different concentrations of deoxyribonucleic acid (DNA) by a sensing device in an embodiment of the invention in Experiment 1.
Figure 4B:
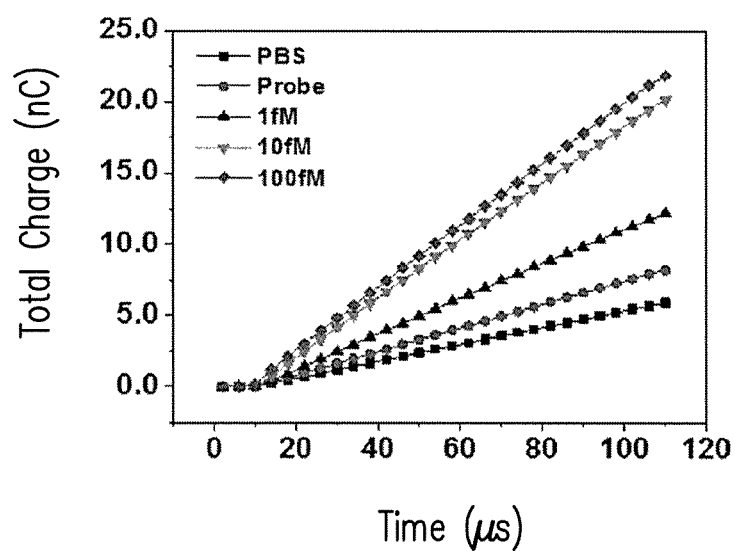
FIG. 4B is a total charge-time graph obtained after performing an integration process on the graph of FIG. 4A.
Figure 4C:
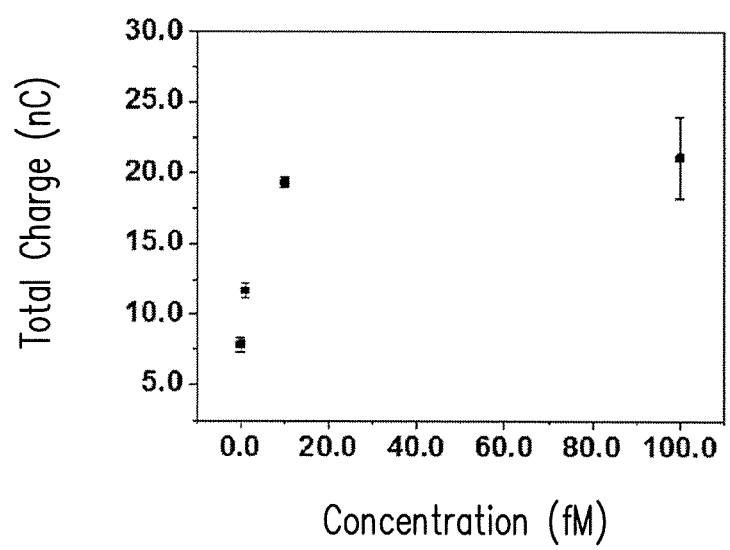
FIG. 4C is a total charge-DNA concentration graph obtained by detecting different concentrations of DNA by the sensing device in an embodiment of the invention in Experiment 1.

FIG. 4A is a current-time graph obtained by detecting different concentrations of DNA by the sensing device in an embodiment of the invention in Experiment 1. FIG. 4B is a total charge-time graph obtained after performing an integration process on the graph of FIG. 4A. FIG. 4C is a total charge-DNA concentration graph obtained by detecting different concentrations of DNA by a sensing device in an embodiment of the invention in Experiment 1.

Note that in order to ensure the receptor is reliably bonded onto an electrode body of the response electrode, a measurement as described below is thereby performed before measuring, so as to ensure that the receptor is reliably bonded onto a surface of the electrode body of the response electrode.

First of all, phosphate buffer solution (PBS) is dropped on the response electrode and the substrate, and the buffer solution covers and is connected to the electrode body of the response electrode and the gate end of the substrate. A voltage is applied to the response electrode, the source end of the transistor is measured, and a current value (the PBS as shown in FIG. 4A) contributed by the phosphate buffer solution is thus obtained. Next, the phosphate buffer solution is removed, and the receptor (e.g., a DNA probe) is dropped onto the electrode body of the response electrode, such that the receptor is bonded onto the response electrode. Then, the phosphate buffer solution is dropped between the response electrode and the substrate, a voltage substantially identical to the aforesaid voltage is applied to the response electrode, the source end of the transistor is measured, and a current value (the Probe as shown in FIG. 4A) contributed by the receptor is thus obtained. With reference to FIG. 4A, the current value (Probe) contributed by the receptor is different from the current value contributed by the phosphate buffer solution (PBS). Therefore, it can be determined that the receptor is reliably bonded onto the response electrode.

Test solutions used in Experiment 1 are test solutions prepared with different DNA concentrations in Tris-ethylenediaminetetraacetic buffer (TE buffer), wherein the DNA concentrations in the TE buffer are 1 fM, 10 fM, and 100 fM, respectively. The results are shown in FIG. 4A to FIG. 4C.

With reference to FIG. 4A and FIG. 4B, as the concentration of DNA becomes higher at the same time, the current (or the total charge) measured by the sensing device shows significant changes. FIG. 4C shows a total charge-concentration graph obtained by detecting the total charges of different DNA concentrations at the same time in FIG. 4B. As shown in FIG. 4C, the sensing device of this embodiment has a detection limit for DNA of 1 fM and has a favorable signal-to-noise ratio (SNR) with respect to the test solution (the Probe shown in FIG. 4A or FIG. 4B may be referenced to) not containing DNA. In view of the above, it can be known that considerably low DNA concentration can still be accurately measured by the sensing device of this embodiment, and even though the test solution is diluted to eliminate interference factors, concentration changes of DNA can still be accurately measured.

Experiment 2

Figure 5A:
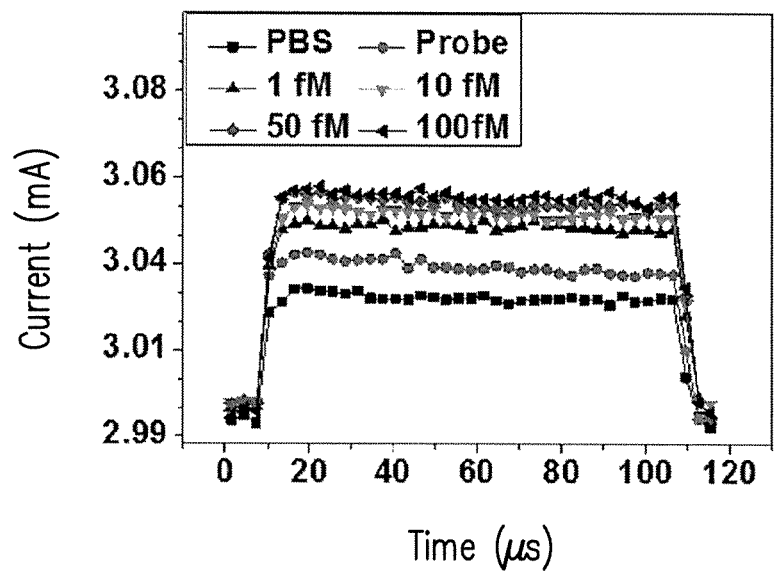
FIG. 5A is a current-time graph obtained by detecting different concentrations of ribonucleic acid (RNA) by the sensing device in an embodiment of the invention in Experiment 2.
Figure 5B:
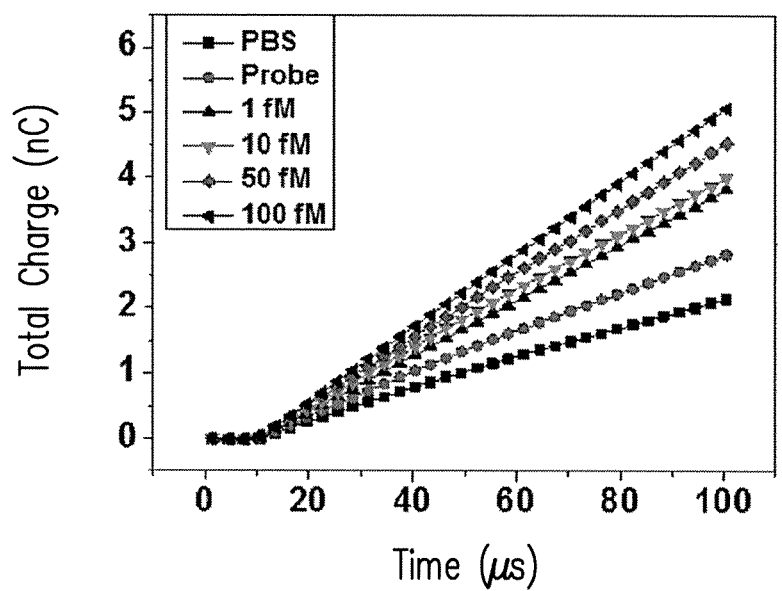
FIG. 5B is a total charge-time graph obtained after performing an integration process on the graph of FIG. 5A.
Figure 5C:
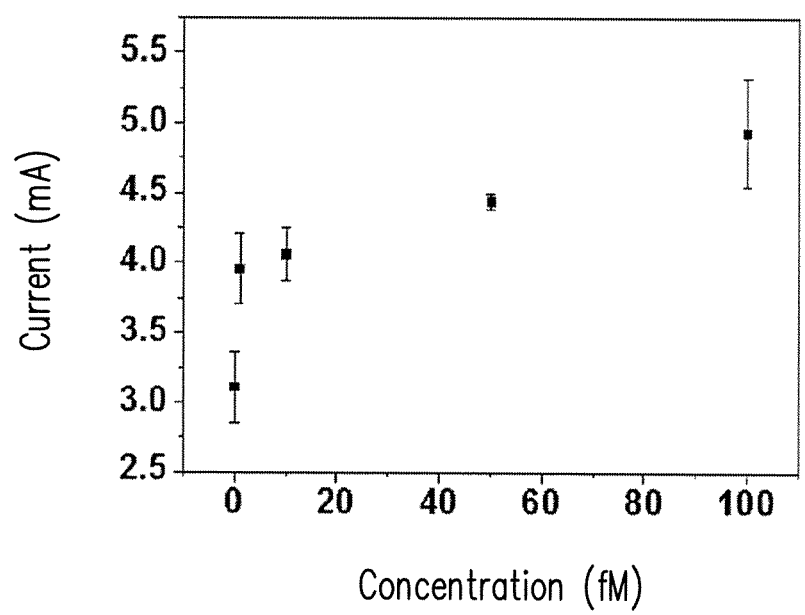
FIG. 5C is a total charge-RNA concentration graph obtained by detecting different concentrations of RNA by the sensing device in an embodiment of the invention in Experiment 2.

FIG. 5A is a current-time graph obtained by detecting different concentrations of ribonucleic acid (RNA) by the sensing device in an embodiment of the invention in Experiment 2. FIG. 5B is a total charge-time graph obtained after performing an integration process on the graph of FIG. 5A. FIG. 5C is a total charge-RNA concentration graph obtained by detecting different concentrations of RNA by the sensing device in an embodiment of the invention in Experiment 2.

Note that in order to ensure the receptor is reliably bonded onto an electrode body of the response electrode, a measurement as described below is thereby performed before measuring, so as to ensure that the receptor is reliably bonded onto a surface of the electrode body of the response electrode.

First of all, phosphate buffer solution (PBS) is dropped on the response electrode and the substrate, and the buffer solution covers and is connected to the electrode body of the response electrode and the gate end of the substrate. A voltage is applied to the response electrode, the source end of the transistor is measured, and a current value (the PBS as shown in FIG. 5A) contributed by the phosphate buffer solution is thus obtained. Next, the phosphate buffer solution is removed, and the receptor (e.g., a ssDNA probe) is dropped onto the electrode body of the response electrode, such that the receptor is bonded onto the response electrode. Then, the phosphate buffer solution is dropped between the response electrode and the substrate, a voltage substantially identical to the foregoing voltage is applied to the response electrode, the source end of the transistor is measured, and a current value (the Probe as shown in FIG. 5A) contributed by the receptor is thus obtained. With reference to FIG. 5A, the current value (Probe) contributed by the receptor is different from the current value contributed by the phosphate buffer solution (PBS). Therefore, it can be determined that the receptor is reliably bonded onto the response electrode.

Test solutions used in Experiment 2 are test solutions prepared with different RNA (miR-208a is used in this experiment) concentrations in Tris-ethylenediaminetetraacetic buffer (TE buffer), wherein the RNA concentrations in the TE buffer are 1 fM, 10 fM, 50 fM, and 100 fM, respectively. The results are shown in FIG. 5A to FIG. 5C.

With reference to FIG. 5A and FIG. 5B, as the concentration of RNA becomes higher at the same time, the current (or the total charge) measured by the sensing device shows significant changes. FIG. 5C shows a total charge-concentration graph obtained by detecting the total charges of different RNA concentrations at the same time in FIG. 5B. As shown in FIG. 5C, the sensing device of this embodiment has a detection limit for RNA of 1 fM and has a favorable signal-to-noise ratio (SNR) with respect to the test solution (the Probe shown in FIG. 5A or FIG. 5B may be referenced to) not containing RNA. In view of the above, it can be known that considerably low RNA concentration can still be accurately measured by the sensing device of this embodiment, and even though the test solution is diluted to eliminate interference factors, concentration changes of RNA can still be accurately measured.

Based on the foregoing embodiments, it can be known that, in the sensing device and the biological detection method proposed in the foregoing embodiments, because the response electrode is disposed opposite to the gate end of the transistor and spaced apart from the transistor, and the electric field between the response electrode and the gate end of the transistor is greater than or equal to 1 mV/cm when a voltage is applied to the response electrode, the sensing device can have the characteristics of the low detection limit and the high sensitivity. Further, because the receptor may be specifically combined with the target substance to be detected, the sensing device can provide a high selectivity for the target substance to be measured.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A sensing device, comprising:
   a transistor comprising a gate end, a source end, a drain end, and a semiconductor layer, wherein the source end and the drain end are located on the semiconductor layer, and the gate end is located between the source end and the drain end; and
   at least one response electrode disposed opposite to the gate end of the transistor and spaced apart from the transistor, wherein the at least one response electrode is not electrically connected to the gate end, wherein the at least one response electrode includes a plurality of receptors bonded to a surface of the at least one response electrode facing the gate end,
   wherein an electric field between the at least one response electrode with the plurality of receptors and the gate end of the transistor is F when a voltage is applied to the at least one response electrode, and F≥1 millivolt/centimeter.

2. The sensing device as claimed in claim 1, wherein the plurality of receptors are spaced apart from each other.

3. The sensing device as claimed in claim 1, wherein each of the plurality of receptors being connected to a corresponding switch of a switch circuit which comprises a plurality of switches.

4. The sensing device as claimed in claim 1, wherein the at least one response electrode is separately disposed above the gate end of the transistor.

5. The sensing device as claimed in claim 1, wherein the at least one response electrode and the gate end of the transistor are located on a same plane.

6. The sensing device as claimed in claim 1, wherein the transistor comprises a high electron mobility transistor, a silicon-based field effect transistor, a nanowire field effect transistor, a carbon nanotube field effect transistor, a graphene field effect transistor, or a molybdenum disulfide field effect transistor.

7. The sensing device as claimed in claim 1, wherein the plurality of receptors comprise antibodies, aptamers, or a combination thereof.

8. The sensing device as claimed in claim 1, wherein the surface on which the at least one response electrode and the plurality of receptors are bonded to each other is formed by gold.

9. A biological detection method, comprising:
   providing a sensing device, wherein the sensing device comprises a transistor and at least one response electrode, the at least one response electrode is disposed opposite to the gate end of the transistor and spaced apart from the transistor, wherein the at least one response electrode is not electrically connected to the gate end, wherein the at least one response electrode includes a plurality of receptors bonded to a surface of the at least one response electrode facing the gate end;
   placing a test solution onto the at least one response electrode, wherein a target substance capable of generating a reaction with the receptor in the test solution is combined on the receptor; and
   applying a voltage to the at least one response electrode to generate an electric field between the at least one response electrode with the plurality of receptors and the gate end of the transistor, and measuring a current generated from the transistor to obtain a content of the target substance in the test solution,
   wherein the electric field is F, and F≥1 millivolt/centimeter.

10. The biological detection method as claimed in claim 9, further comprising:
    enabling the target substance and the receptor to perform a hybridization reaction at a hybridization temperature after placing the test solution onto the at least one response electrode.

11. The biological detection method as claimed in claim 10, further comprising:
    enabling the target substance and the receptor to perform a dehybridization reaction at a dehybridization temperature after applying a voltage to the at least one response electrode.

12. The biological detection method as claimed in claim 11, wherein the dehybridization temperature is greater than the hybridization temperature, and the hybridization temperature is less than or equal to $T_m$ values of the receptor and the target substance.

13. The biological detection method as claimed in claim 9, wherein the plurality of receptors are spaced apart from each other.

14. The biological detection method as claimed in claim 9, wherein each of the plurality of receptors being connected to a corresponding switch of a switch circuit which comprises a plurality of switches.

15. The biological detection method as claimed in claim 9, wherein the at least one response electrode is separately disposed above the gate end of the transistor.

16. The biological detection method as claimed in claim 9, wherein the at least one response electrode and the gate end of the transistor are formed on a same plane.

17. The biological detection method as claimed in claim 9, wherein the transistor comprises a high electron mobility transistor, a silicon-based field effect transistor, a nanowire field effect transistor, a carbon nanotube field effect transistor, a graphene field effect transistor, or a molybdenum disulfide field effect transistor.

18. The biological detection method as claimed in claim 9, wherein the plurality of receptors comprise antibodies, aptamers, or a combination thereof.

19. The biological detection method as claimed in claim 9, wherein the surface on which the at least one response electrode and the plurality of receptors are bonded to each other is formed by gold.

20. The biological detection method as claimed in claim 9, wherein the target substance comprises deoxyribonucleic acid, ribonucleic acid, or a combination thereof.

21. The sensing device as claimed in claim 1, wherein the transistor further comprising:
    a protective layer disposed on top surfaces and sidewalls of the source end and the drain end, and exposing the gate end facing to the surface of the at least one response electrode.

* * * * *